US007653492B2

(12) United States Patent
Davies et al.

(10) Patent No.: US 7,653,492 B2
(45) Date of Patent: *Jan. 26, 2010

(54) METHOD OF REDUCING THE EFFECT OF DIRECT INTERFERENCE CURRENT IN AN ELECTROCHEMICAL TEST STRIP

(75) Inventors: Oliver William Hardwicke Davies, Croy (GB); Robert Marshall, Conon Bridge (GB); Damian Edward Haydon Baskeyfield, Auldeam (GB); Lynsey Whyte, Lochardil (GB); Elaine Leiper, Inverness (GB)

(73) Assignee: Lifescan Scotland Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/577,586

(22) PCT Filed: Oct. 29, 2004

(86) PCT No.: PCT/GB2004/004574

§ 371 (c)(1),
(2), (4) Date: Apr. 26, 2006

(87) PCT Pub. No.: WO2005/045412

PCT Pub. Date: May 19, 2005

(65) Prior Publication Data

US 2007/0276621 A1    Nov. 29, 2007

Related U.S. Application Data

(60) Provisional application No. 60/516,252, filed on Oct. 31, 2003, provisional application No. 60/558,424, filed on Mar. 31, 2004, provisional application No. 60/558,728, filed on Mar. 31, 2004.

(51) Int. Cl.
*G01N 31/00*    (2006.01)

(52) U.S. Cl. .......................... 702/22; 702/23
(58) Field of Classification Search .................. 702/17, 702/22, 23, 104, 189–191, 25, 50, 64, 65, 702/100; 204/403.01, 403.11, 403.14; 205/775, 205/779; 600/345, 347
See application file for complete search history.

(56) References Cited

U.S. PATENT DOCUMENTS 4,431,004 A    2/1984    Bessman et al.

(Continued)

FOREIGN PATENT DOCUMENTS

WO    WO 89/02593 A1    3/1989

(Continued)

OTHER PUBLICATIONS

Matsue et al., "Multichannel electrochemical detection system for flow analysis", 1990, pp. 407-409.*

(Continued)

*Primary Examiner*—Michael P Nghiem

(57) ABSTRACT

This invention describes a method of reducing the effect of interfering compounds in a bodily fluid when measuring an analyte using an electrochemical sensor. In particular, the present method is applicable to electrochemical sensors where the sensor includes a substrate, first and second working electrodes, and a reference electrode and either the first and second or only the second working electrode include regions which are bare of reagent. In this invention, an algorithm is described with mathematically corrects for the interference effect using the test strip embodiments of the present invention.

10 Claims, 11 Drawing Sheets

U.S. PATENT DOCUMENTS

| | | | |
|---|---|---|---|
| 4,655,880 A | 4/1987 | Liu et al. | |
| 5,298,146 A | 3/1994 | Braden et al. | |
| 5,582,697 A | 12/1996 | Ikeda et al. | |
| 5,628,890 A | 5/1997 | Carter et al. | |
| 5,650,062 A | 7/1997 | Ikeda et al. | |
| 5,653,918 A | 8/1997 | Towlson | |
| 5,708,247 A | 1/1998 | McAleer et al. | |
| 5,830,343 A | 11/1998 | Hintsche et al. | |
| 5,985,116 A | 11/1999 | Ikeda et al. | |
| 6,046,051 A | 4/2000 | Jina | |
| 6,212,417 B1 | 4/2001 | Ikeda et al. | |
| 6,258,229 B1 | 7/2001 | Winarta et al. | |
| 6,287,451 B1 | 9/2001 | Winarta et al. | |
| 6,540,891 B1 | 4/2003 | Stewart et al. | |
| 6,730,200 B1 | 5/2004 | Stewart et al. | |
| RE38,681 E * | 1/2005 | Kurnik et al. | 205/777.5 |
| 7,132,041 B2 * | 11/2006 | Deng et al. | 205/777.5 |
| 2002/0092612 A1* | 7/2002 | Davies et al. | 156/292 |
| 2002/0157947 A1 | 10/2002 | Rappin et al. | |
| 2002/0168290 A1 | 11/2002 | Yuzhakov et al. | |
| 2003/0143113 A2 | 7/2003 | Yuzhakov et al. | |
| 2004/0149578 A1* | 8/2004 | Huang | 204/403.01 |
| 2005/0023136 A1* | 2/2005 | Leach et al. | 204/403.01 |
| 2005/0109618 A1* | 5/2005 | Davies | 204/400 |
| 2005/0114062 A1* | 5/2005 | Davies et al. | 702/104 |
| 2005/0139469 A1* | 6/2005 | Davies et al. | 204/403.01 |
| 2005/0139489 A1* | 6/2005 | Davies et al. | 205/775 |
| 2005/0183965 A1* | 8/2005 | Davies | 205/775 |
| 2009/0029479 A1* | 1/2009 | Docherty et al. | 436/149 |

FOREIGN PATENT DOCUMENTS

| | | |
|---|---|---|
| WO | WO 99/13099 A1 | 3/1999 |
| WO | WO 00/13099 A1 | 3/2000 |
| WO | WO 00/79258 A1 | 12/2000 |
| WO | WO 01/67099 A1 | 9/2001 |
| WO | WO 01/73124 A2 | 10/2001 |
| WO | WO 02/49507 A1 | 6/2002 |
| WO | WO2004/029605 A1 | 4/2004 |
| WO | WO 2004/039600 A2 | 5/2004 |
| WO | 2005045412 * | 5/2005 |

OTHER PUBLICATIONS

Harrington M. S. et al. "Multiple Electrode Potentiostat" Review of Scientific Instruments, American Institute of Physics. New York, US, vol. 60, No. 10, Oct. 1, 1989, pp. 3323-3328, XP000071728 ISSN: 0034-6748.

* cited by examiner

METHOD OF REDUCING THE EFFECT OF DIRECT INTERFERENCE CURRENT IN AN ELECTROCHEMICAL TEST STRIP

PRIORITY

The present invention claims priority to the following U.S. Provisional Applications: U.S. Provisional Application Ser. No. 60/516,262 filed on Oct. 31, 2003; U.S. Provisional Application Ser. No. 60/558,424 filed on Mar. 31, 2004; U.S. Provisional Application Ser. No. 60/558,728 filed on Mar. 31, 2004; and to the following International Application Number PCT/GB2004/004574 filed on Oct. 29, 2004; which applications are hereby incorporated herein by reference.

RELATED APPLICATIONS

The present invention is related to the following co-pending U.S. application Ser. Nos. 10/977,292, filed Oct. 29, 2004, now abandoned; 10/977,154, filed Oct. 29, 2004, now allowed; 10/977,155, filed Oct. 29, 2004; 10/976,489, filed Oct. 29, 2004, now abandoned; 10/977,316, filed Oct. 29, 2004, now abandoned; and 10/977,086, filed Oct. 29, 2004, now abandoned.

FIELD OF THE INVENTION

The present invention is related, in general to methods of reducing the effect of interfering compounds on measurements taken by analyte measurement systems and, more particularly, to a method of reducing the effects of direct interference currents in a glucose monitoring system using an electrochemical strip having electrodes with uncoated regions.

BACKGROUND OF INVENTION

In many cases, an electrochemical glucose measuring system may have an elevated oxidation current due to the oxidation of interfering compounds commonly found in physiological fluids such as, for example, acetaminophen, ascorbic acid, bilirubin, dopamine, gentisic acid, glutathione, levodopa, methyldopa, tolazimide, tolbutamide, and uric acid. The accuracy of glucose meters may, therefore, be improved by reducing or eliminating the portion of the oxidation current generated by interfering compounds. Ideally, there should be no oxidation current generated from any of the interfering compounds so that the entire oxidation current would depend only on the glucose concentration.

It is, therefore, desirable to improve the accuracy of electrochemical sensors in the presence of potentially interfering compounds such as, for example, ascorbate, urate, and, acetaminophen, commonly found in physiological fluids. Examples of analytes for such electrochemical sensors may include glucose, lactate, and fructosamine. Although glucose will be the main analyte discussed, it will be obvious to one skilled in the art that the invention set forth herein may also be used with other analytes.

Oxidation current may be generated in several ways. In particular, desirable oxidation current results from the interaction of the redox mediator with the analyte of interest (e.g., glucose) while undesirable oxidation current is generally comprised of interfering compounds being oxidized at the electrode surface and by interaction with the redox mediator. For example, some interfering compounds (e.g., acetomiphen) are oxidized at the electrode surface. Other interfering compounds (e.g., ascorbic acid), are oxidized by chemical reaction with the redox mediator. This oxidation of the interfering compound in a glucose measuring system causes the measured oxidation current to be dependent on the concentration of both the glucose and any interfering compound. Therefore, in the situation where the concentration of interfering compound oxidizes as efficiently as glucose and the interferent concentration is high relative to the glucose concentration, the measurement of the glucose concentration would be improved by reducing or eliminating the contribution of the interfering compounds to the total oxidation current.

One known strategy that can be used to decrease the effects of interfering compounds is to use a negatively charged membrane to cover the working electrode. As an example, a sulfonated fluoropolymer such as NAFION™ may be used to repel all negatively charged chemicals. In general, most interfering compounds such as ascorbate and urate have a negative charge, thus, the negatively charged membrane prevents the negatively charged interfering compounds from reaching the electrode surface and being oxidized at the surface. However, this technique is not always successful since some interfering compounds such as acetaminophen do not have a net negative charge, and thus, can pass through a negatively charged membrane. Nor would this technique reduce the oxidation current resulting from the interaction of interfering compounds with some redox mediators. The use of a negatively charged membrane on the working electrode could also prevent some commonly used redox mediators, such as ferricyanide, from passing through the negatively charged membrane to exchange electrons with the electrode.

Another known strategy that can be used to decrease the effects of interfering compounds is to use a size selective membrane on top of the working electrode. As an example, a 100 Dalton exclusion membrane such as cellulose acetate may be used to cover the working electrode to exclude all chemicals with a molecular weight greater than 100 Daltons. In general, most interfering compounds have a molecular weight greater than 100 Daltons, and thus, are excluded from being oxidized at the electrode surface. However, such selective membranes typically make the test strip more complicated to manufacture and increase the test time because the oxidized glucose must diffuse through the selective membrane to get to the electrode.

Another strategy that can be used to decrease the effects of interfering compounds is to use a redox mediator with a low redox potential, for example, between about −300 mV and +100 mV (when measured with respect to a saturated calomel electrode). Because the redox mediator has a low redox potential, the voltage applied to the working electrode may also be relatively low which, in turn, decreases the rate at which interfering compounds are oxidized by the working electrode. Examples of redox mediators having a relatively low redox potential include osmium bipyridyl complexes, ferrocene derivatives, and quinone derivatives. A disadvantage of this strategy is that redox mediators having a relatively low potential are often difficult to synthesize, unstable and have a low water solubility.

Another known strategy that can be used to decrease the effects of interfering compounds is to use a dummy electrode which is coated with a redox mediator. In some instances the dummy electrode may also be coated with an inert protein or deactivated redox enzyme. The purpose of the dummy electrode is to oxidize the interfering compound at the electrode surface and/or to oxidize the redox mediator reduced by the interfering compound. In this strategy, the current measured at the dummy electrode is subtracted from the total oxidizing current measured at the working electrode to remove the interference effect. A disadvantage of this strategy is that it requires that the test strip include an additional electrode and electrical connection (i.e., the dummy electrode) which cannot be used to measure glucose. The inclusion of dummy electrode is an inefficient use of an electrode in a glucose measuring system.

SUMMARY OF INVENTION

The invention described herein is directed to a method of reducing the effects of interferences when using an electrochemical sensor to detect analytes. An electrochemical sensor, which would be useable in a method according to the present invention, includes a substrate, at least first and second working electrodes and a reference electrode. A reagent layer is disposed on the electrodes such that the reagent layer completely covers all of the first working electrode and only partially covers the second working electrode. In a method according to the present invention, the oxidation current generated at the portion of the second working electrode not covered by the reagent layer is used to correct for the effect of interfering substances on the glucose measurement.

The invention described herein further includes a method of reducing interferences in an electrochemical sensor, including the steps of measuring a first oxidation current at a first working electrode, where the first working electrode is covered by a reagent layer; measuring a second oxidation current at a second working electrode, where the reagent layer only partially covers the second working electrode; and calculating a corrected oxidation current value representative of a concentration of a pre-selected analyte (e.g., glucose). In this calculation, a ratio of the covered area to the uncovered area of the second working electrode is used to remove the effects of interferences on the oxidation current. More particularly, the corrected current value may be calculated using the following equation, $$G = WE_1 - \left\{ \left( \frac{A_{cov}}{A_{unc}} \right) \times (WE_2 - WE_1) \right\}$$

where G is the corrected current density, $WE_1$ is the uncorrected current density at the first working electrode, $WE_2$ is the uncorrected current density at the second working electrode, $A_{cov}$ is the coated area of the second working electrode, and $A_{unc}$ is the uncoated area of the second working electrode 2.

In one embodiment of an electrochemical strip useable in the present invention, the electrochemical glucose test strip includes a first and second working electrodes, where the first working electrode is completely covered with a reagent layer and the second working electrode is only partially covered with the reagent layer. Thus, the second working electrode has a reagent coated area and an uncoated area. The reagent layer may include, for example, a redox enzyme such as glucose oxidase and a redox mediator such as, for example, ferricyanide. The first working electrode will have a superposition of two oxidation current sources, one from glucose and a second from interferents. Similarly, the second working electrode will have a superposition of three oxidation current sources from glucose, interferents at the reagent coated portion, and interferents at the uncoated portion. The uncoated portion of the second working electrode will only oxidize interferents and not oxidize glucose because there is no reagent is in this area. The oxidation current measured at the uncoated portion of the second working electrode may then be used to estimate the total interferent oxidation current and calculate a corrected oxidation current which removes the effects of interferences.

In an alternative strip embodiment useable in the method according to the present invention, the electrochemical glucose test strip includes a first and second working electrodes, where the first and second working electrode are only partially covered with the reagent layer. Thus, in this embodiment both the first and second working electrode have a reagent coated portion and an uncoated portion. The first uncovered area of the first working electrode and the second uncovered area of the second working electrode are different. The oxidation current measured at the uncoated portion of the first and second working electrodes are used to estimate the interferent oxidation current for the uncoated portion and to calculate a corrected glucose current.

The invention described herein further includes a method of reducing interferences in an electrochemical sensor, including the steps of measuring a first oxidation current at a first working electrode, where the first working electrode is partially covered by a reagent layer; measuring a second oxidation current at a second working electrode, where the reagent layer only partially covers the second working electrode; and calculating a corrected oxidation current value representative of a concentration of a pre-selected analyte (e.g., glucose). In this calculation, a ratio of the covered area to the uncovered area of the first and second working electrodes is used to remove the effects of interferences on the oxidation current. More particularly, the corrected current value may be calculated using the following equation $$G = WE_1 - \left\{ \left( \frac{f_1 + f_2}{f_2 - 1} \right) \times (WE_2 - WE_1) \right\}$$

where f1 is equal to $$\frac{A_{cov1}}{A_{unc1}};$$

f2 is equal to $$\frac{A_{cov1}}{A_{unc2}};$$

$A_{unc1}$ is the uncoated area of the first working electrode; $A_{unc2}$ is the uncoated area of the second working electrode; $A_{cov1}$ is the coated area of said first working electrode; $A_{cov2}$ is the coated area of the second working electrode; G is the corrected current value; $WE_1$ is the uncorrected current density at the first working electrode; and $WE_2$ is the uncorrected current density at the second working electrode.

BRIEF DESCRIPTION OF DRAWINGS

A better understanding of the features and advantages of the present invention will be obtained by reference to the following detailed description that sets forth illustrative embodiments, in which the principles of the invention are utilized, and the accompanying drawings, of which.

DETAILED DESCRIPTION OF THE INVENTION

This invention described herein includes a test strip and method for improving the selectivity of an electrochemical glucose measuring system.

Figure 1:
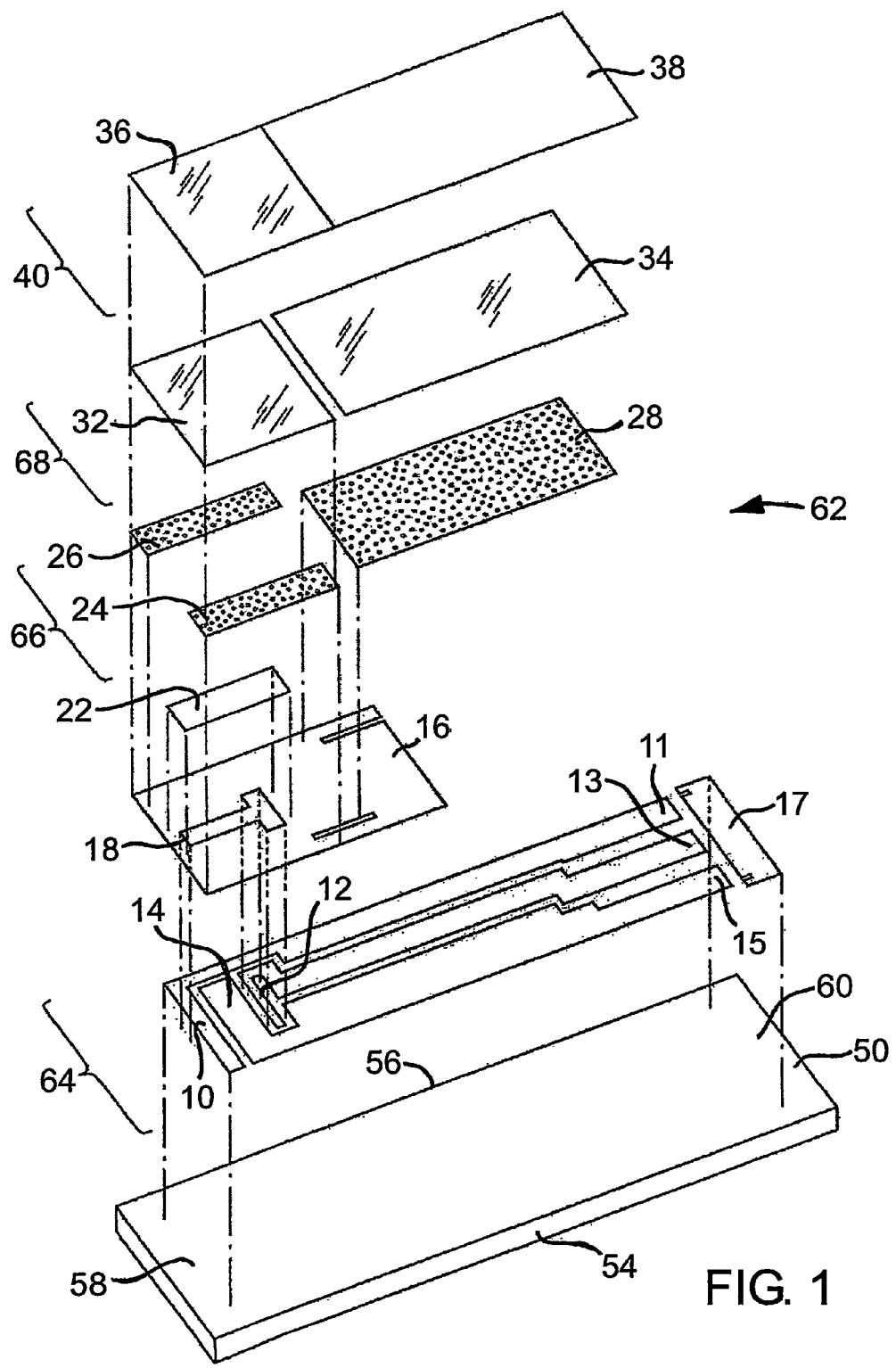
FIG. 1 is an exploded perspective view of a test strip according to a embodiment of the present invention.

FIG. 1 is an exploded perspective view of a test strip according to a first embodiment of the present invention. In the embodiment of the present invention illustrated in FIG. 1, an electrochemical test strip 62, which may be used for measuring glucose concentration in bodily fluids such as blood or interstitial fluid, includes a first working electrode 10 and a second working electrode 12, where first working electrode 10 is completely covered with a reagent layer 22 and second working electrode 12 is only partially covered with reagent layer 22. Thus, the second working electrode has a reagent coated portion and an uncoated portion. Reagent layer 22 may include, for example, a redox enzyme such as, for example, glucose oxidase and a redox mediator such as, for example, ferricyanide. Because ferricyanide has a redox potential of approximately 400 mV (when measured with respect to a saturated calomel electrode) at a carbon electrode, the introduction of a bodily fluid e.g., blood may generate a significant oxidation of interferents by the redox mediator and/or the working electrode generating a significant undesirable oxidation current. Therefore, the oxidation current measured at first working electrode 10 will be a superposition of oxidation current sources: a first, desirable, oxidation current generated by the oxidation of glucose and a second, undesirable, oxidation current generated by the interferents. The oxidation current measured at second working electrode 12 will also be a superposition of oxidation current sources: a first, desirable oxidation current generated by the oxidation of glucose, a second, undesirable oxidation current generated by interferents at the covered portion of working electrode 12 and a third oxidation current generated by interferents at the uncovered portion of working electrode 12. The uncoated portion of second working electrode 12 will only oxidize interferents and not oxidize glucose because there is no reagent on the uncoated portion of second working electrode 12. Because the oxidation current measured at the uncoated portion of second working electrode 12 does not depend on glucose and the uncoated area of second working electrode 12 is known, it is possible to calculate the interferent oxidation current for the uncoated portion of the second working electrode 12. In turn, using the interferent oxidating current calculated for the uncoated portion of second working electrode 12 and knowing the are of first working electrode 10 and the area of the coated portion of second working electrode 12, it is possible to calculate a corrected glucose current which accounts for the effects of interfering compounds oxidized at the electrode.

FIG. 1 is an exploded perspective view of a test strip 62 according to a first embodiment of the present invention. Test strip 62, as illustrated in FIG. 1, may be manufactured by a series of 6 consecutive printing steps which lay down six layers of material on substrate 50. The six layers may be deposited by, for example, screen printing on substrate 50. In an embodiment of this invention, the 6 layers may include a conductive layer 64, an insulation layer 16, a reagent layer 22, an adhesive layer 66, a hydrophilic layer 68, and a top layer 40. Conductive layer 64 may further includes first working electrode 10, second working electrode 12, reference electrode 14, first contact 11, second contact 13, reference contact 15, and strip detection bar 17. Insulation layer 16 may further include cutout 18. Adhesive layer 66 may further include first adhesive pad 24, second adhesive pad 26, and third adhesive pads 28. Hydrophilic layer 68 may further include first hydrophilic film 32, and second hydrophilic film 34. Top layer 40 may further includes a clear portion 36 and opaque portion 38. Test strip 62 has a first side 54 and second side 56, a distal electrode side 58, and a proximal electrode side 60 as illustrated in FIG. 1. The following sections will describe the respective layers of test strip 62 in more detail.

In one embodiment of the present invention, substrate 50 is an electrically insulating material such as plastic, glass, ceramic, and the like. In a preferred embodiment of this invention, substrate 50 may be a plastic such as, for example nylon, polycarbonate, polyimide, polyvinylchloride, polyethylene, polypropylene, PETG, or polyester. More particularly the polyester may be, for example Melinex® ST328 which is manufactured by DuPont Teijin Films. Substrate 50 may also include an acrylic coating which is applied to one or both sides to improve ink adhesion.

The first layer deposited on substrate 50 is conductive layer 64 which includes first working electrode 10, second working electrode 12, reference electrode 14, and strip detection bar 17. In accordance with the present invention, a screen mesh with an emulsion pattern may be used to deposit a material such as, for example, a conductive carbon ink in a defined geometry as illustrated in FIG. 1. Reference electrode 14 may also be a counter electrode, a reference/counter electrode, or a quasi-reference electrode. Conductive layer 64 may be disposed on substrate 50 by using screen printing, rotogravure printing, sputtering, evaporation, electroless plating, ink jetting, sublimation, chemical vapor deposition, and the like. Suitable materials which may be used for conductive layer 64 are Au, Pd, Ir, Pt, Rh, stainless steel, doped tin oxide, carbon, and the like. In an embodiment of this invention, the carbon ink layer may have a height between 1 and 100 microns, more particularly between 5 and 25 microns, and yet even more particularly at approximately 13 microns. The height of the conductive layer can vary depending on the desired resistance of the conductive layer and the conductivity of the material used for printing the conductive layer.

First contact 11, second contact 13, and reference contact 15 may be used to electrically interface with a meter. This allows the meter to electrically communicate to first working electrode 10, second working electrode 12, and reference electrode 14 via, respectively, first contact 11, second contact 13, and reference contact 15.

Figure 2:
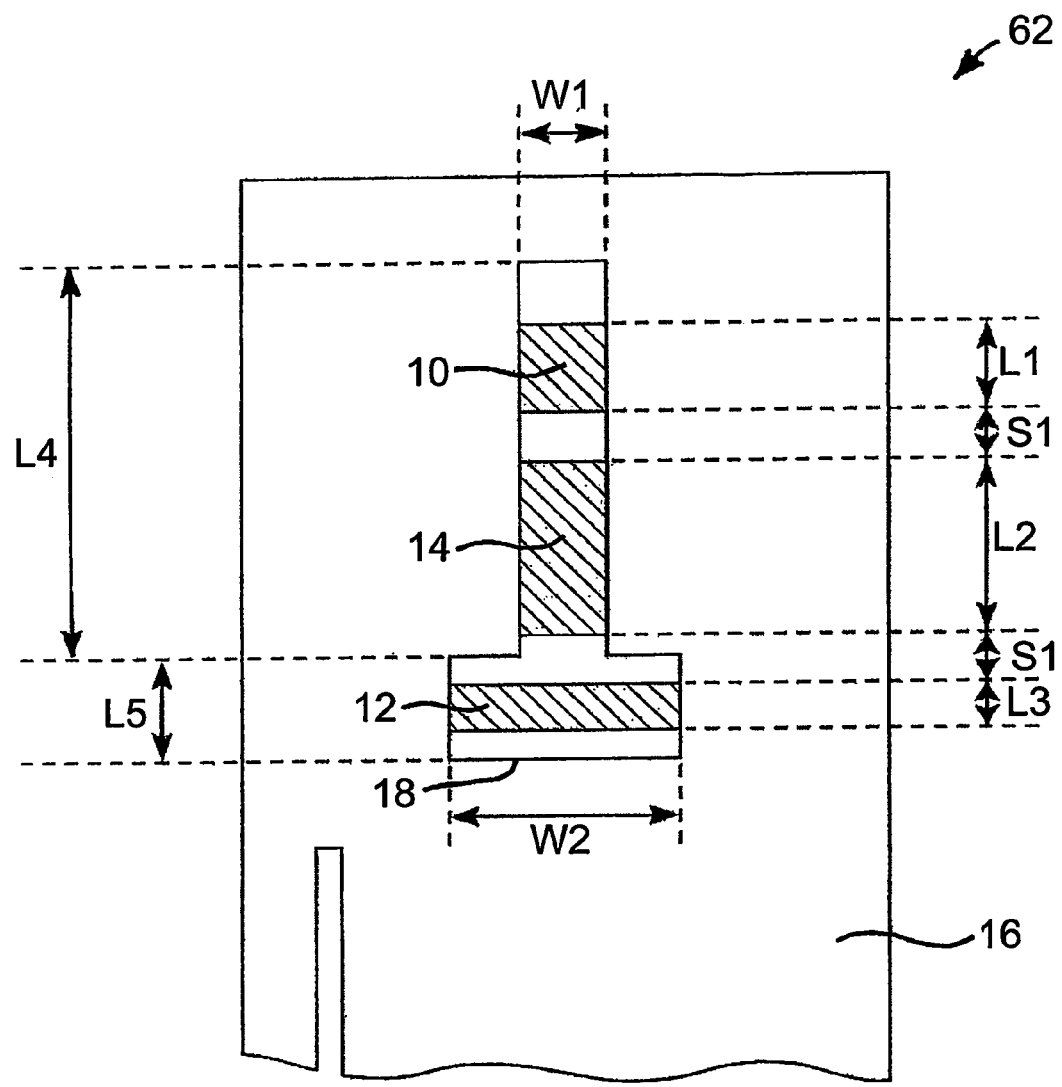
FIG. 2 is a simplified plane view of a distal portion of a test strip according to the embodiment of the present invention illustrated in FIG. 1 including a conductive layer and an insulation layer.

The second layer deposited on substrate 50 is insulation layer 16. Insulation layer 16 is disposed on at least a portion of conductive layer 64 as shown in FIG. 1. FIG. 2 is a simplified plane view of a distal portion of test strip 62 which highlights the position of first working electrode 10, second working electrode 12, and reference electrode 14 with respect to insulation layer 16. Insulation layer 16 further includes a cutout 18 which may have a T-shaped structure as shown in FIGS. 1 and 2. Cutout 18 exposes a portions of first working electrode 10, second working electrode 12, and reference electrode 14 which can be wetted with liquid. Cutout 18 further includes a distal cutout width W1, proximal cutout width W2, a distal cutout length L4 and a proximal cutout length L5. Distal cutout width W1 corresponds to the width of first working electrode 10 and reference electrode 14 as illustrated in FIG. 2. Distal cutout length L4 corresponds to a length which is greater than both first working electrode 10 and reference electrode 14 together. Proximal cutout width W2 and proximal cutout length L5 form a rectangular section which exposes the width and length of second working electrode 12. In accordance with the present invention, distal cutout width W1, proximal cutout width W2, distal cutout length L4 and proximal cutout length L5 may have a respective dimension of approximately 0.7, 1.9, 3.2, and 0.43 mm. In one embodiment of the present invention, first working electrode 10, reference electrode 14, and second working electrode 12 have a respective length of L1, L2, and L3 which may be about 0.8, 1.6, and 0.4 mm. In accordance with the present invention, electrode spacing S1 is a distance between first working electrode 10 and reference electrode 14; and between reference electrode 14 and second working electrode 12 which may be about 0.4 mm.

Figure 3:
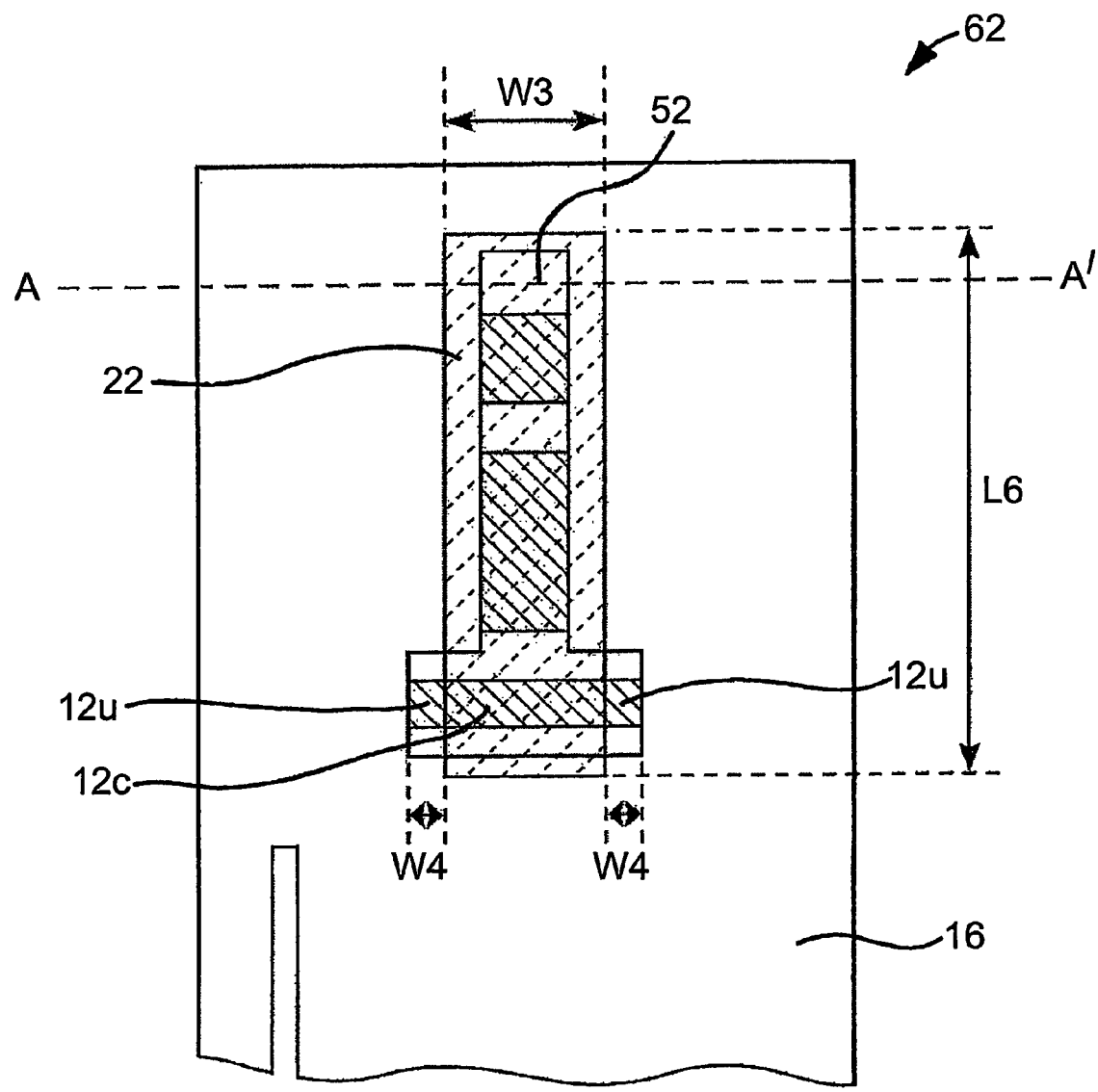
FIG. 3 is a simplified plane view of a distal portion of a test strip according to the embodiment of the present invention illustrated in FIG. 1 wherein the position of a reagent layer is illustrated with the conductive layer and the insulation layer.

The third layer deposited on substrate 50 is a reagent layer 22. Reagent layer 22 is disposed on at least a portion of conductive layer 64 and insulation layer 16 as shown in FIG. 1. FIG. 3 is a simplified plane view of a distal portion of test strip 62 according to the first embodiment of the present invention which highlights the position of reagent layer 22 with respect to first working electrode 10, second working electrode 12, reference electrode 14 and insulation layer 16. Reagent layer 22 may be in the shape of a rectangle having a reagent width W3 and a reagent length L6 as illustrated in FIGS. 1 and 3. In one embodiment of the invention, reagent width W3 may be about 1.3 mm and reagent length L6 may be about 4.7 mm. In a further embodiment of the present invention, reagent layer 22 has a sufficiently large width W3 and length L6 such that reagent layer 22 completely covers first working electrode 10 and reference electrode 14. However, reagent layer 22 has an appropriately sized width W3 and length L6 such that second working electrode is not completely covered with reagent layer 22. In such a scenario, second working electrode 12 has a coated portion 12c and an uncoated portions 12u as illustrated in FIG. 3. Uncoated portions 12u may be in the shape of two rectangles where uncoated portions 12u has a wing width W4 and a length that corresponds to second working electrode length L3. As a non-limiting example, wing width W4 may be about 0.3 mm. In one embodiment of the present invention, reagent layer 22 may include a redox enzyme such as, for example, glucose oxidase or PQQ-glucose dehydrogenase (where PQQ is an acronym for pyrrolo-quinoline-quinone) and a redox mediator such as, for example, ferricyanide.

The fourth layer deposited on substrate 50 is an adhesive layer 66 which includes a first adhesive pad 24, a second adhesive pad 26, and third adhesive pad 28. First adhesive pad 24 and second adhesive pad 26 form the walls of a sample receiving chamber. In one embodiment of the present invention, first adhesive pad 24 and second adhesive pad 26 may be disposed on substrate 50 such that neither of the adhesive pads touches reagent layer 22. In another embodiments of the present invention where the strip volume needs to be reduced, first adhesive pad 24 and/or second adhesive pad 26 may be disposed on substrate 50 such there is overlap with reagent layer 22. In an embodiment of the present invention, adhesive layer 66 has a height of about 70 to 110 microns. Adhesive layer 66 may include a double sided pressure sensitive adhesive, a UV cured adhesive, heat activated adhesive, thermosetting plastic, or other adhesive known to those skilled in the art. As a non-limiting example, adhesive layer 66 may be formed by screen printing a pressure sensitive adhesive such as, for example, a water based acrylic copolymer pressure sensitive adhesive which is commercially available from Tape Specialties LTD in Tring, Herts, United Kingdom (part#A6435).

The fifth layer deposited on substrate 50 is a hydrophilic layer 68 which includes a first hydrophilic film 32 second hydrophilic film 34 as illustrated in FIG. 1. Hydrophilic layer 68 forms the "roof" of the sample receiving chamber. The "side walls" and "floor" of the sample receiving chamber are formed by a portion of the adhesive layer 66 and substrate 50, respectively. As a non-limiting example, hydrophilic layer 68 may be an optically transparent polyester with a hydrophilic anti-fog coating such as those commercially obtained from 3M. The hydrophilic nature of the coating is used in the design of strip 62 because it facilitates filling of liquid into the sample receiving chamber.

The sixth and final layer deposited on substrate 50 is a top layer 40 which includes a clear and opaque portion (36 and 38) as illustrated in FIG. 1. In accordance with the present invention, top layer 40 includes a polyester which is coated on one side with a pressure sensitive adhesive. Top layer 40 has an opaque portion 38 which helps the user observe a high degree of contrast when blood is underneath clear portion 36. This allows a user to visually confirm that the sample receiving chamber is sufficiently filled. After strip 62 is fully laminated, it is cut along incision line A-A' and in the process creates sample inlet 52 as illustrated in FIG. 3.

The first test strip embodiment as illustrated in FIGS. 1-3 may have a possible drawback in that reagent layer 22 may dissolve in a liquid sample and move a portion of the dissolved reagent layer over the uncoated portions 12u of second working electrode 12. If such a scenario were to occur, uncoated portions 12u would also measure an oxidation current that is also proportional to the glucose concentration. This would degrade the ability to use mathematical algorithms for removing the effect of interferent oxidation. In an alternative embodiment of the present invention, reagent layer 22 should be designed to dissolve in such a way that it does not migrate to uncoated portions 12u. For example, reagent layer 22 may be chemically bound to the first working electrode 10, second working electrode 12, and reference electrode 14 or may have a thickening agent that minimizes the migration of dissolved reagent layer 22.

Figure 4:
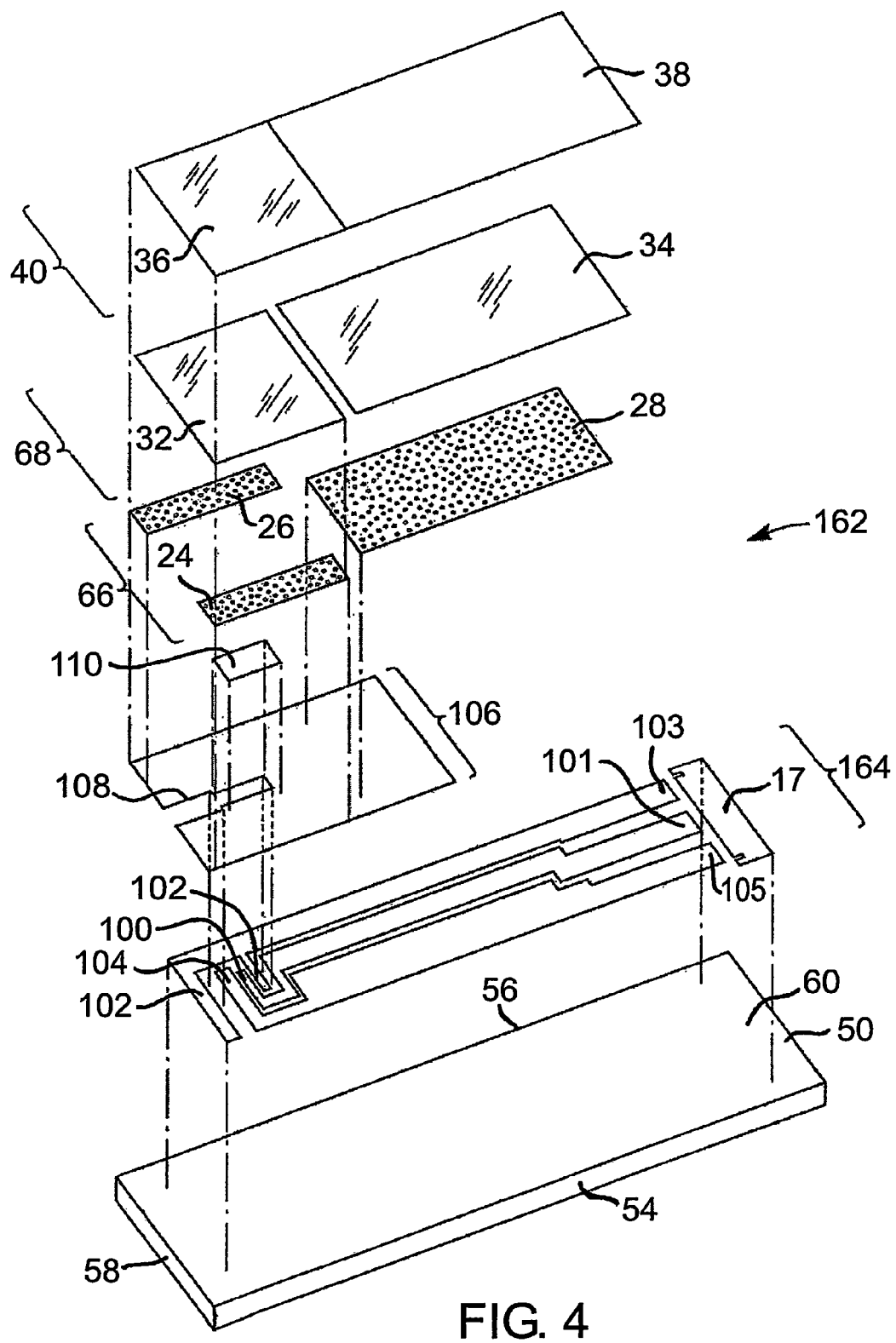
FIG. 4 is an exploded perspective view of a test strip according to a further embodiment of the present invention.
Figure 6:
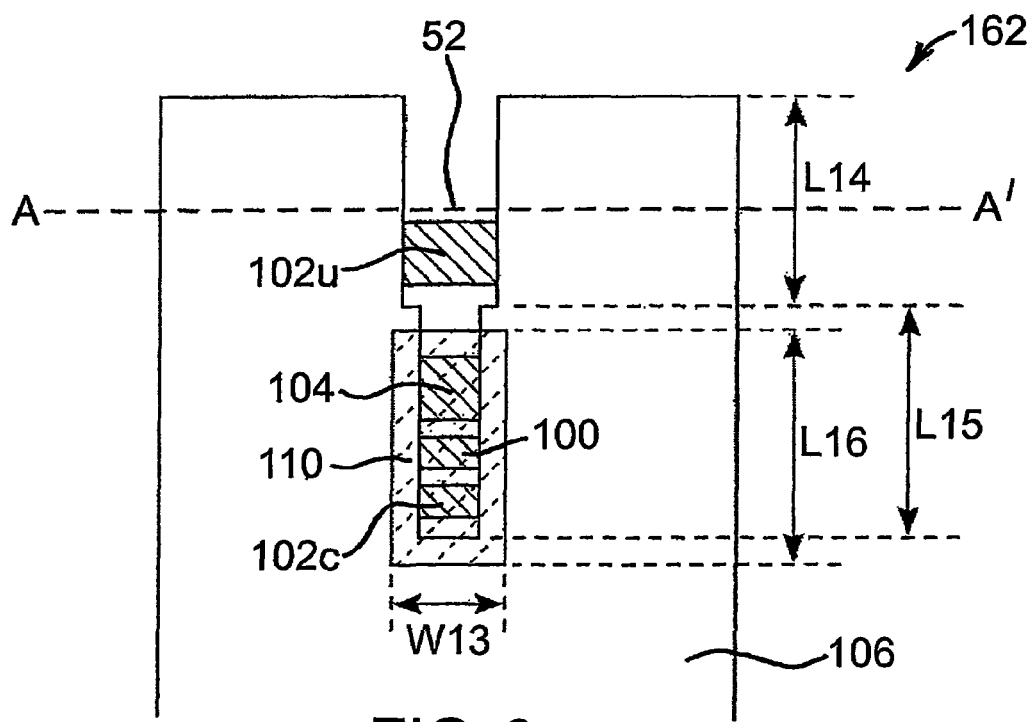
FIG. 6 is a simplified plane view of a distal portion of a test strip according to the embodiment of the present invention illustrated in FIG. 4 wherein a reagent layer is illustrated with the conductive layer and the insulation layer.

A further embodiment of the present invention as illustrated in FIG. 4, the embodiment illustrated in FIG. 4 reduces, and in certain circumstances minimizes, the immigration of dissolved reagent to an uncoated portion of the second working electrode. In this embodiment, second working electrode 102 has a C-shaped geometry where 2 discrete portions of second working electrode 102 are exposed by cutout 108 as illustrated in FIG. 4. In accordance with the present invention, reagent layer 110 is disposed on only a portion of second working electrode 102 to form an uncoated portion 102u and coated portion 102c as illustrated in FIG. 6. Uncoated portion 102u is adjacent to sample inlet 52. Coated portion 102c is adjacent to first working electrode 100. When applying liquid to sample inlet 52 of an assembled test strip 162, the liquid will flow from sample inlet 52 to coated portion 102c until all electrodes are covered with liquid. By positioning uncoated portion 102u upstream of the liquid flow, this almost entirely prevents reagent layer 110 from dissolving and migrating to uncoated portion 102u. This enables the mathematical algorithm to accurately remove the effects of interferents from the measured oxidation current.

FIG. 4 is an exploded perspective view of a test strip 162. Test strip 162 is manufactured in a manner similar to test strip 62 except that there are geometric or positional changes to a conductive layer 164, an insulation layer 106, and a reagent layer 102. For the second embodiment of this invention, substrate 50, adhesive layer 66, hydrophilic layer 68, and top layer 40 are the same as the first strip embodiment. Test strip 162 has a first side 54 and second side 56, a distal electrode side 58, and a proximal electrode side 60. It should also be noted that the first and second test strip embodiment of the present invention may have elements with similar structure which are denoted with the same element number and name. If analogous elements between the respective test strip embodiments are different in structure, the elements may have the same name, but be denoted with a different element number. The following sections will describe the respective layers of test strip 162 in more detail.

For the strip embodiment illustrated in FIG. 4, the first layer deposited on substrate 50 is conductive layer 164 which includes first working electrode 100, second working electrode 102, reference electrode 104, first contact 101, second contact 103, and reference contact 105, and strip detection bar 17. In accordance with the present invention, a screen mesh with an emulsion pattern may be used to deposit a material such as, for example, a conductive carbon ink in a defined geometry as illustrated in FIG. 4. First contact 101, second contact 103, and reference contact 105 may be used to electrically interface with a meter. This allows the meter to electrically communicate to first working electrode 100, second working electrode 102, and reference electrode 104 via, respective, first contact 101, second contact 103, and reference contact 105.

Figure 5:
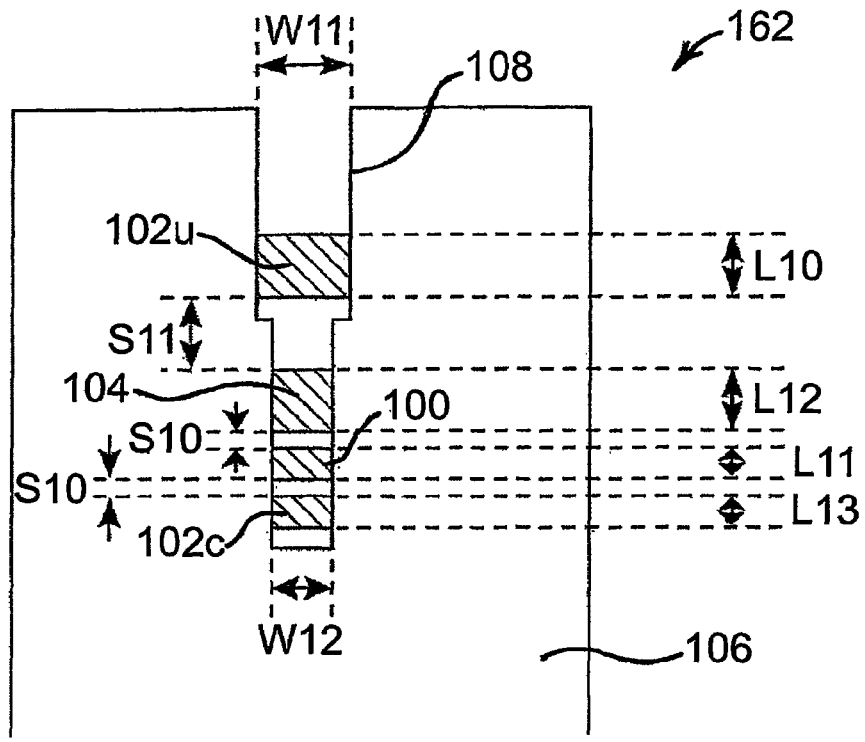
FIG. 5 is a simplified plane view of a distal portion of a test strip according to the embodiment of the present invention illustrated in FIG. 4 including of a conductive layer and an insulation layer.

The second layer deposited on substrate 50 in FIG. 4 is insulation layer 106. Insulation layer 106 is disposed on at least a portion of conductive layer 164 as shown in FIG. 4. FIG. 5 is a simplified plane view of a distal portion of test strip 162 which highlights the position of first working electrode 100, second working electrode 102, and reference electrode 104 with respect to insulation layer 106.

The third layer deposited on substrate 50 in FIG. 4 is a reagent layer 110 such that reagent layer 110 is disposed on at least a portion of conductive layer 164 and insulation layer 106 as shown in FIG. 6. FIG. 6 is a simplified plane view of a distal portion of test strip 162 according to the second embodiment of the present invention which highlights the position of reagent layer 110 with respect to first working electrode 100, second working electrode 102, reference electrode 104, and insulation layer 106. Reagent layer 110 may be in the shape of a rectangle having a reagent width W13 and a reagent length L16. In one embodiment of this invention, reagent width W13 may be about 1.3 mm and reagent length L16 may be about 3.2 mm. In a preferred embodiment of the present invention, reagent layer 110 has a sufficient width W13 and length L16 such that reagent layer 110 completely covers first working electrode 100, coated portion 102c, and reference electrode 104, but does not cover uncoated portion 102u.

Figure 7:
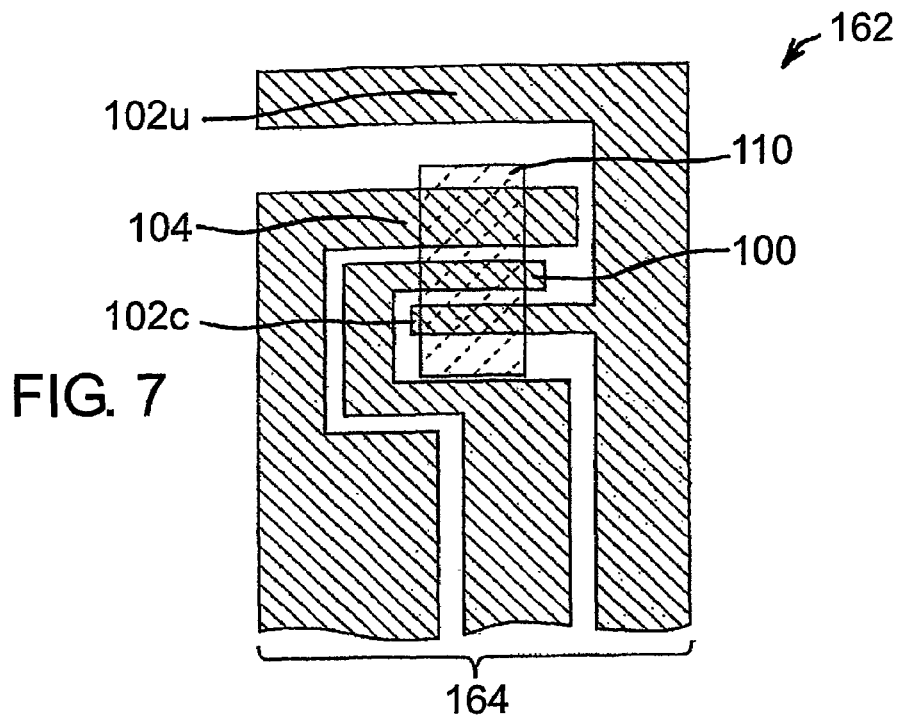
FIG. 7 is a simplified plane view of a distal portion of a test strip according to the embodiment of the present invention illustrated in FIG. 4 wherein a reagent layer is illustrated with the conductive layer.
Figure 8:
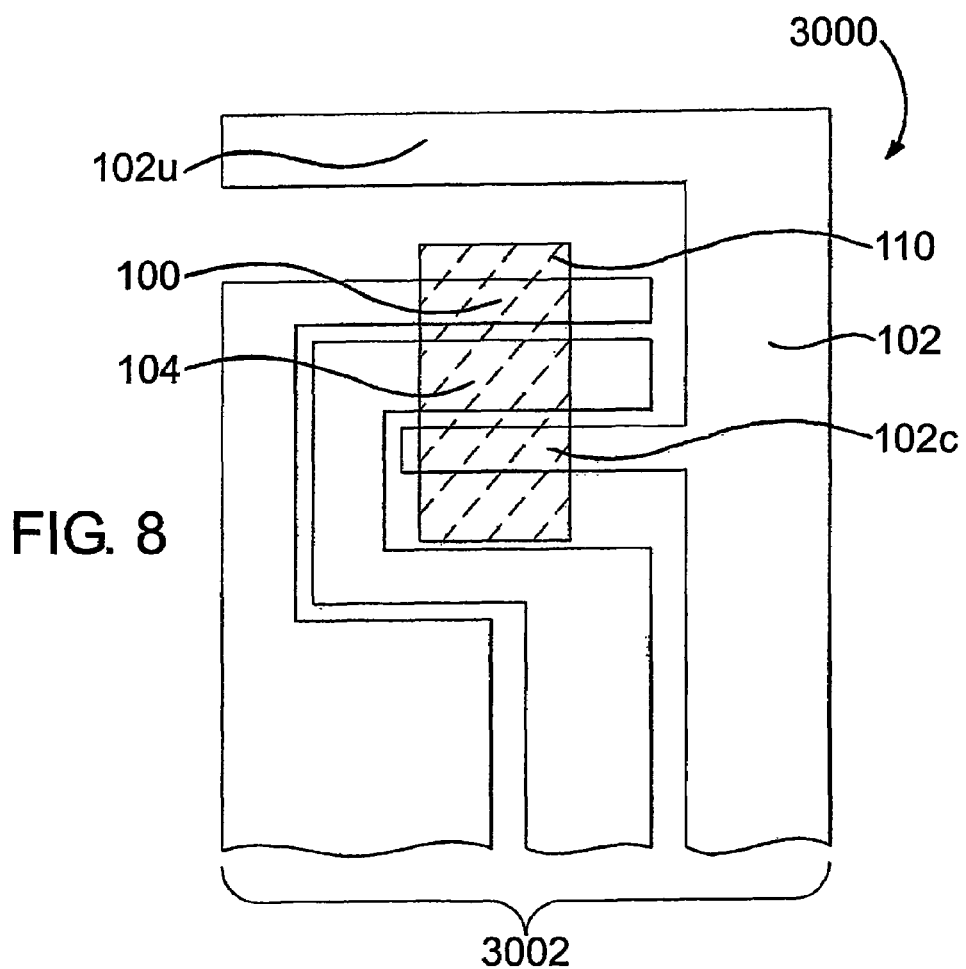
FIG. 8 is a simplified plane view of a distal portion of a test strip according to another embodiment of the present invention wherein a reagent layer is illustrated with the conductive layer that helps reduce an IR drop effect.

FIG. 7 is a simplified plane view of a distal portion of a test strip according to the embodiment of the present invention illustrated in FIG. 4 wherein a reagent layer is illustrated with the conductive layer. In contrast to FIG. 6, FIG. 7 does not show insulation layer 106. This helps demonstrate the conductive relationship between uncoated portion 102u and coated portion 102c which was hidden underneath the opaque character of illustration layer 106.

For the strip embodiment illustrated in FIG. 4, insulation layer 106 is used to define the width of the first working electrode 100, second working electrode 102, and reference electrode 104. Insulation layer 106 further includes a cutout 108 which may have a T-shaped structure as shown in FIGS. 4 to 6. Cutout 108 exposes a portion of first working electrode 100, second working electrode 102, and reference electrode 104 which can be wetted with liquid. Cutout 108 further includes a distal cutout width W11, proximal cutout width W12, a distal cutout length L14 and a proximal cutout length L15 as illustrated in FIGS. 5 and 6. Distal cutout width W11 corresponds to the width of uncoated portion 102u. Distal cutout length L14 is greater than the length uncoated portion 102u. Proximal cutout width W12 and proximal cutout length L15 forms a rectangular section which approximately exposes the width and length of first working electrode 100, reference electrode 104, and coated portion 102c.

In accordance with the present invention, distal cutout width W11, proximal cutout width W12, distal cutout length L14 and proximal cutout length L15 may have a respective dimension of approximately 1.1, 0.7, 2.5, and 2.6 mm.

In the embodiment of FIG. 4, uncoated portion 102u, reference electrode 104, first working electrode 100, and coated portion 102c have a respective length of L11, L12, L11, and L13 which may be about 0.7, 0.7, 0.4, and 0.4 mm. Electrode spacing S11 is a distance between uncoated portion 102u and reference electrode 104 which may be between about 0.2 to 0.75 mm, and more preferably between 0.6 to 0.75 mm. Electrode spacing S10 is a distance between reference electrode 104 and first working electrode 100; and between coated portion 102c and first working electrode 100 which may be about 0.2 mm. It should be noted that electrode spacing S11 is greater than S10 to decrease the possibility of reagent dissolving and migrating to uncoated portion 102u. Additionally, electrode spacing S11 is greater than S10 to decrease the possibility of reagent layer 110 being disposed on uncoated portion 102u because of variations in the printing process. The fourth through sixth layer which is successively disposed on strip 162 in the same manner as the first strip embodiment. The relative position and shape of the adhesive layer 66, hydrophilic layer 68, and top layer 40 are illustrated in FIG. 4.

In an alternative embodiment to the second strip embodiment, the C-shape of second working electrode 102 may be partially altered so that the order in which liquid would wet the electrodes would be uncoated portion 102u, first working electrode 100, reference electrode 104, and then coated portion 102c. In the alternative format, first working electrode 100 and coated portion 102c would be equidistant from reference electrode 100 which is desirable from an IR drop perspective. In the second strip embodiment (i.e. test strip 162) illustrated in FIG. 7, the electrodes are arranged so that the order in which liquid would wet the electrodes would be uncoated portion 102u, reference electrode 104, first working electrode 100, and then coated portion 102c. For test strip 162, coated portion 102c is farther away from reference electrode 104 than the distance between first working electrode 100 and reference electrode 104.

An algorithm may, therefore be used to calculate a corrected glucose current that is independent of interferences. After dosing a sample onto a test strip, a constant potential is applied to the first and second working electrodes and a current is measured for both electrodes. At the first working electrode where reagent covers the entire electrode area, the following equation can be used to describe the components contributing to the oxidation current, $$WE_1 = G + I_{cov} \tag{Eq 1}$$

where $WE_1$ is the current density at first working electrode, G is the current density due to glucose which is independent of interferences, and $I_{cov}$ is the current density due to interferences at the portion of a working electrode covered with reagent.

At the second working electrode which is partially covered with reagent, the following equation can be used to describe the components contributing to the oxidation current, $$WE_2 = G + I_{cov} + I_{unc} \tag{Eq 2}$$

where $WE_2$ is the current density at second working electrode and $I_{unc}$ is the current density due to interferences at the portion of a working electrode not covered with reagent. Alternative embodiments of the present invention can be made using different areas of reagent coating for the first and second working electrode, but then the equations must account for the different uncoated areas.

To reduce the effects of interferences, an equation is formulated which describes the relationship between the interferent current at the coated portion of the second working electrode and the uncoated portion of the second working electrode. It is approximated that the interferent oxidation current density measured at the coated portion is the same as the current density measured at the uncoated portion. This relationship is further described by the following equation, $$I_{cov} = \frac{A_{cov}}{A_{unc}} \times I_{unc} \tag{Eq 3a}$$

where $A_{cov}$ is the area of second working electrode covered with reagent and $A_{unc}$ is the area of second working electrode not covered with reagent.

It should be noted that uncoated portions 12u and coated portions 12u may have a respective area denoted as $A_{unc}$ and $A_{cov}$. Uncoated portions 12u can oxidize interferents, but not glucose because it is not coated with reagent layer 22. In contrast, coated portion 12c can oxidize glucose and interferents. Because it was experimentally found that uncoated portions 12u oxidizes interferents in a manner proportional to the area of coated portion 12c, it is possible to predict the proportion of interferent current measured overall at second working electrode. This allows the overall current measured at second working electrode 12 to be corrected by subtracting the contribution of the interferent current. In an embodiment of the present invention the ratio of $A_{unc}:A_{cov}$ may be between about 0.5:1 to 5:1, and is preferably about 3:1. More details describing this mathematical algorithm for current correction will be described in a later section.

In an alternative embodiment of the present invention, the interferent oxidation current density measured at the coated portion may be different than the current density measured at the uncoated portion. This may be ascribed to a more efficient or less efficient oxidation of interferents at the coated portion. In one scenario, the presence of a redox mediators may enhance the oxidation of interferences relative to the uncoated portion. In another scenario, the presence of viscosity increasing substances such as hydroxyethyl cellulose may decrease the oxidation of interferences relative to the uncoated portion. Depending on the components included in the reagent layer which partially coats the second working electrode, it is possible that the interferent oxidation current density measured at the coated portion may be more or less than the uncoated portion. This behavior may be phenomenologically modeled by re-writing Equation 3a to the following form, $$I_{cov} = f \times I_{unc} \tag{Eq 3b}$$

where $f$ is a correction factor which incorporates the effects of the interferent oxidation efficiency of the coated to uncoated portion.

In an embodiment of the present invention, Equation 1, 2, and 3a may be manipulated to derive an equation that outputs a corrected glucose current density independent of interferences. It should be noted that the three equations (Equation 1, 2, and 3a) collectively have 3 unknowns which are G, $I_{cov}$, and $I_{unc}$. Equation 1 can be rearranged to the following form.

$$G = WE_1 - I_{cov} \tag{Eq 4}$$

Next, $I_{cov}$ from Equation 3a can be substituted into Equation 4 to yield Equation 5.

$$G = WE_1 - \left[\frac{A_{cov}}{A_{unc}} \times I_{unc}\right] \tag{Eq 5}$$

Next, Equation 1 and Equation 2 can be combined to yield Equation 6.

$$I_{unc} = WE_2 - WE_1 \tag{Eq 6}$$

Next, $I_{unc}$ from Equation 6 can be substituted into Equation 5 to yield Equation 7a.

$$G = WE_1 - \left\{\left(\frac{A_{cov}}{A_{unc}}\right) \times (WE_2 - WE_1)\right\}$$ (Eq 7a)

Equation 7a outputs a corrected glucose current density G which removes the effects of interferences requiring only the current density output of the first and second working electrode, and a proportion of the coated to uncoated area of the second working electrode. In one embodiment of the present invention the proportion $$\frac{A_{cov}}{A_{unc}};$$

may be programmed into a glucose meter, in, for example, a read only memory. In another embodiment of the present invention, the proportion $$\frac{A_{cov}}{A_{unc}};$$

may be transferred to the meter via a calibration code chip which would may account for manufacturing variations in $A_{cov}$ or $A_{unc}$.

In the alternative embodiment to the present invention Equation 1, 2, and 3b may be used when the interferent oxidation current density for the coated portion is different than the interferent oxidation current density of the uncoated portion. In such a case, an alternative correction Equation 7b is derived as shown below.

$$G = WE_1 - \{f \times (WE_2 - WE_1)\}$$ (Eq 7b)

In another embodiment of the present invention, the corrected glucose current Equation 7a or 7b may be used by the meter only when a certain threshold is exceeded. For example, if $WE_2$ is about 10% or greater than $WE_1$, then the meter would use Equation 7a or 7b to correct for the current output. However, if $WE_2$ is about 10% or less than $WE_1$, the meter would simple take an average current value between $WE_1$ and $WE_2$ to improve the accuracy and precision of the measurement. The strategy of using Equation 7a or 7b only under certain situations where it is likely that a significant level of interferences are in the sample mitigates the risk of overcorrecting the measured glucose current. It should be noted that when $WE_2$ is sufficiently greater than $WE_1$ (e.g. about 20% or more), this is an indicator of having a sufficiently high concentration of interferences. In such a case, it may be desirable to output an error message instead of a glucose value because a very high level of interferents may cause a breakdown in the accuracy of Equation 7a or 7b.

Figure 10:
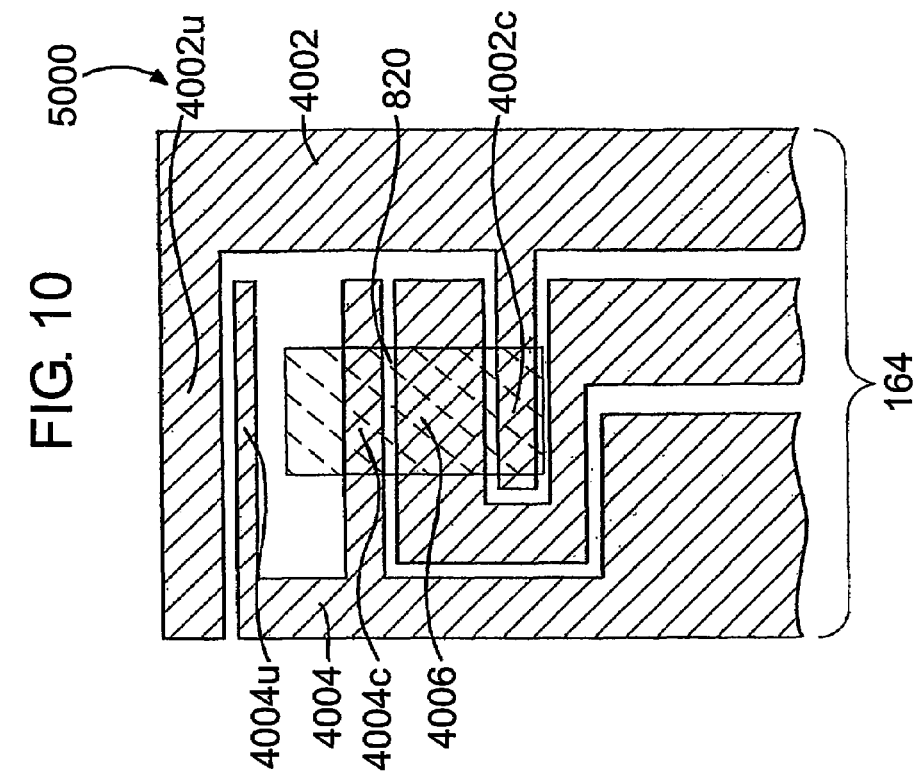
FIG. 10 is a simplified plane view of a distal portion of a test strip according to still yet another embodiment of the present invention wherein a reagent layer is illustrated with the conductive layer and the insulation layer such there are two working electrodes that have an uncoated portion.
Figure 9:
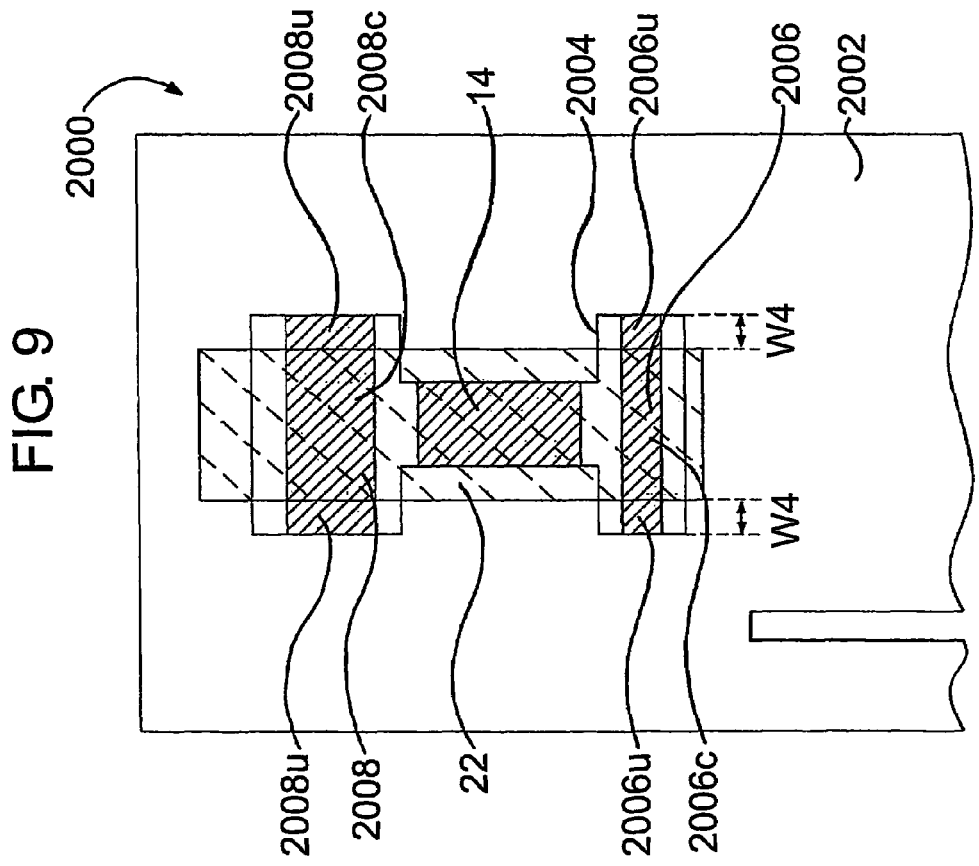
FIG. 9 is a simplified plane view of a distal portion of a test strip according to yet another embodiment of the present invention wherein a reagent layer is illustrated with the conductive layer and the insulation layer such there are two working electrodes that have an uncoated portion.

In the embodiment of the present invention illustrated in FIGS. 9 and 10, the first and second working electrodes are partially covered with the reagent layer in such a way that that the uncoated portions of the first and second working electrodes are different. This contrasts the previously described first and second test strip embodiments where the first working electrode is completely covered with the reagent layer.

FIG. 9 is a simplified plane view of a distal portion of a test strip 2000 according to yet another embodiment of the present invention wherein a reagent layer 22 is illustrated with the conductive layer and insulation layer 2002 such there are two working electrodes which have an uncoated portion. Test strip 2002 is manufactured in a manner similar to test strip 62 except that there is a geometric change to cutout 18 as shown in FIG. 1. Test strip 2002 has the same substrate 50, conductive layer 64, reagent layer 22, adhesive layer 66, hydrophilic layer 68, and top layer 40 as test strip 62. Test strip 2002 was modified to have a cutout 2004 which has a dumbbell like shape as illustrated in FIG. 9. The modified shape for cutout 2004 allows first working electrode 2008 to include a first coated portion 2008c and an first uncoated portion 2008u; and second working electrode 2006 to include a second coated portion 2006c and second uncoated portion 2006u. In order for test strip 2000 to effectively reduce the effects of interferents, first uncoated portion 2008u must have a different total area than second uncoated portion 2006u.

FIG. 10 is a simplified plane view of a distal portion of a test strip 5000 according to still yet another embodiment of the present invention wherein a reagent layer 820 is illustrated with the conductive layer such there are two working electrodes which have an uncoated portion. Test strip 5000 is manufactured in a manner similar to test strip 162 except that there is a geometric change to conductive layer 164 such that both a first working electrode 4002 and a second working electrode 4004 have a c-shape. Test strip 5000 has the same substrate 50, insulation layer 106, reagent layer 110, adhesive layer 66, hydrophilic layer 68, and top layer 40 as test strip 162. The modified geometry allows first working electrode 4002 to include a first coated portion 4002c and a first uncoated portion 4002u; and second working electrode 4004 to include a second coated portion 4004c and second uncoated portion 4004u. In order for test strip 2000 to effectively reduce the effects of interferents, first uncoated portion 4002u must have a different area than second uncoated portion 4004u.

Test strips 2000 and 5000 have an advantage in that they may be easier to manufacture in regards to depositing the reagent layer with the required registration and also any subsequently deposited layers. Furthermore, both the first and second working electrodes will have to some extent the same chemical and electrochemical interactions with any interfering substances thus ensuring greater accuracy in the correction process. With both working electrodes having some level of uncoated area the same reactions will occur on both electrodes but to a different extent. Using a simple modification to Equation 7a, the following Equation 7c can be used as the correction equation for glucose, $$G = WE_1 - \left\{\left(\frac{f_1 + f_2}{f_2 - 1}\right) \times (WE_2 - WE_1)\right\}$$ (Eq 7c)

where $$f_1 = \frac{A_{cov1}}{A_{unc1}}, f_2 = \frac{A_{cov1}}{A_{unc2}},$$

$A_{unc1}$=is an uncoated area of the first working electrode,
$A_{unc2}$=is an uncoated area of the second working electrode,
$A_{cov1}$=is a coated area of the first working electrode, and
$A_{cov2}$=is a coated area of the second working electrode.

One advantage of the present invention is the ability to use the first and second working electrode to determine that the sample receiving chamber has been sufficiently filled with liquid. It is an advantage of this invention in that the second working electrode not only corrects the interferent effect, but can also measure glucose. This allows for a more accurate result because 2 glucose measurements can be averaged together while using only one test strip.

Example 1

Test strips were prepared according to the first embodiment of the present invention as illustrated in FIGS. 1 to 3. These test strips were tested in blood having various concentrations of interferents. To test these strips, they were electrically connected to a potentiostat which has the means to apply a constant potential of 0.4 volts between the first working electrode and the reference electrode; and the second working electrode and the reference electrode. A sample of blood is applied to the sample inlet allowing the blood to wick into the sample receiving chamber and to wet first working electrode, second working electrode, and reference electrode. The reagent layer becomes hydrated with blood and then generates ferrocyanide which may be proportional to the amount of glucose and/or interferent concentration present in the sample. After about 5 seconds from the sample application to the test strip, an oxidation of ferrocyanide is measured as a current for both the first and second working electrode.

Figure 11:
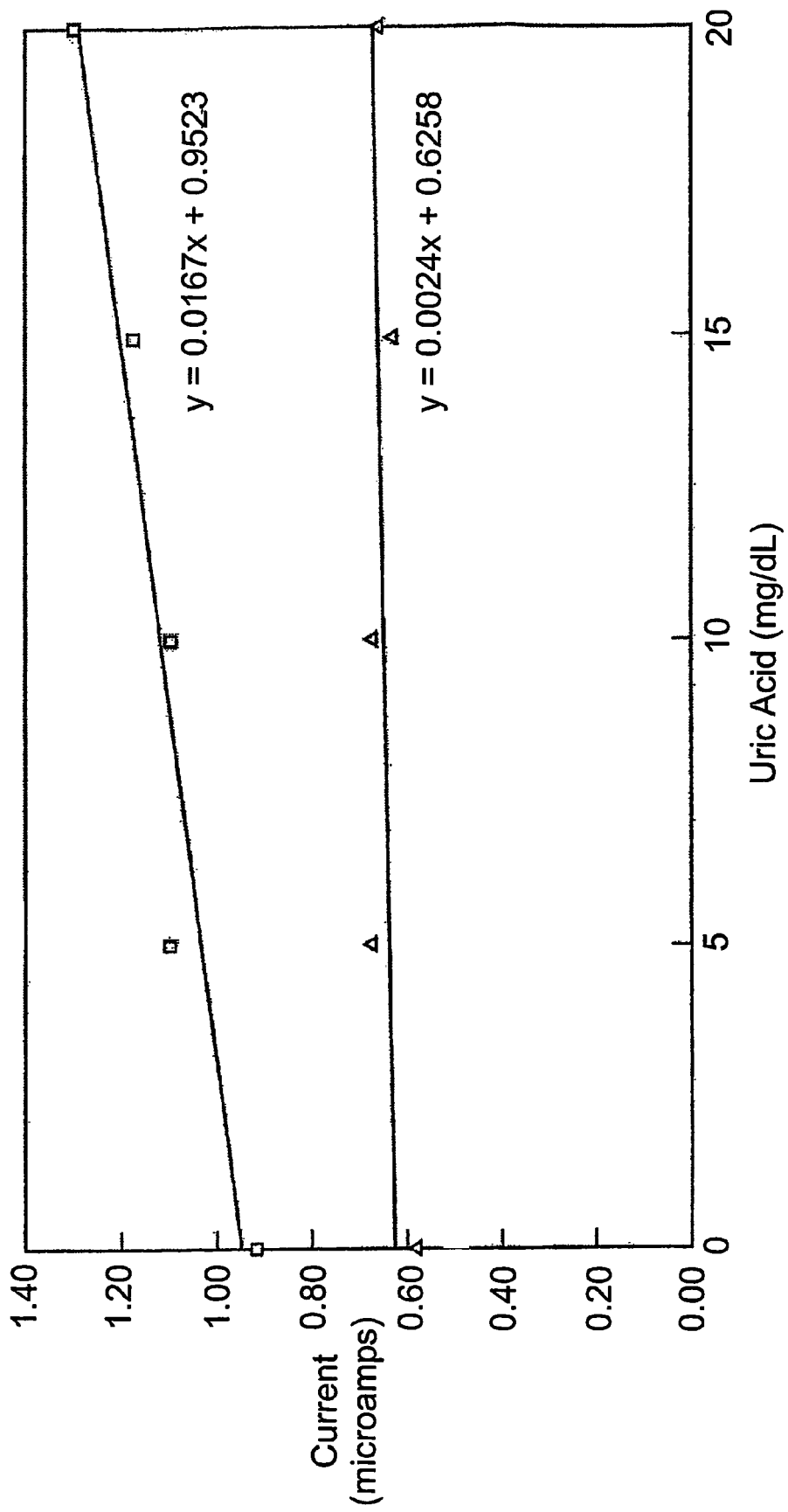
FIG. 11 is a graph showing the current at a first working electrode of a strip designed in accordance with the present invention tested with 70 mg/dL glucose samples in blood spiked with varying levels of uric acid.

FIG. 11 shows the current responses of the first working electrode tested with 70 mg/dL glucose samples in blood spiked with varying levels of uric acid. The uncorrected current at the first working electrode (depicted by squares) shows an increase in current that is proportional to the uric acid concentration. However, the corrected current (depicted by triangles) which is processed by Equation 7a shows no effect from the increasing uric acid concentration.

Figure 12:
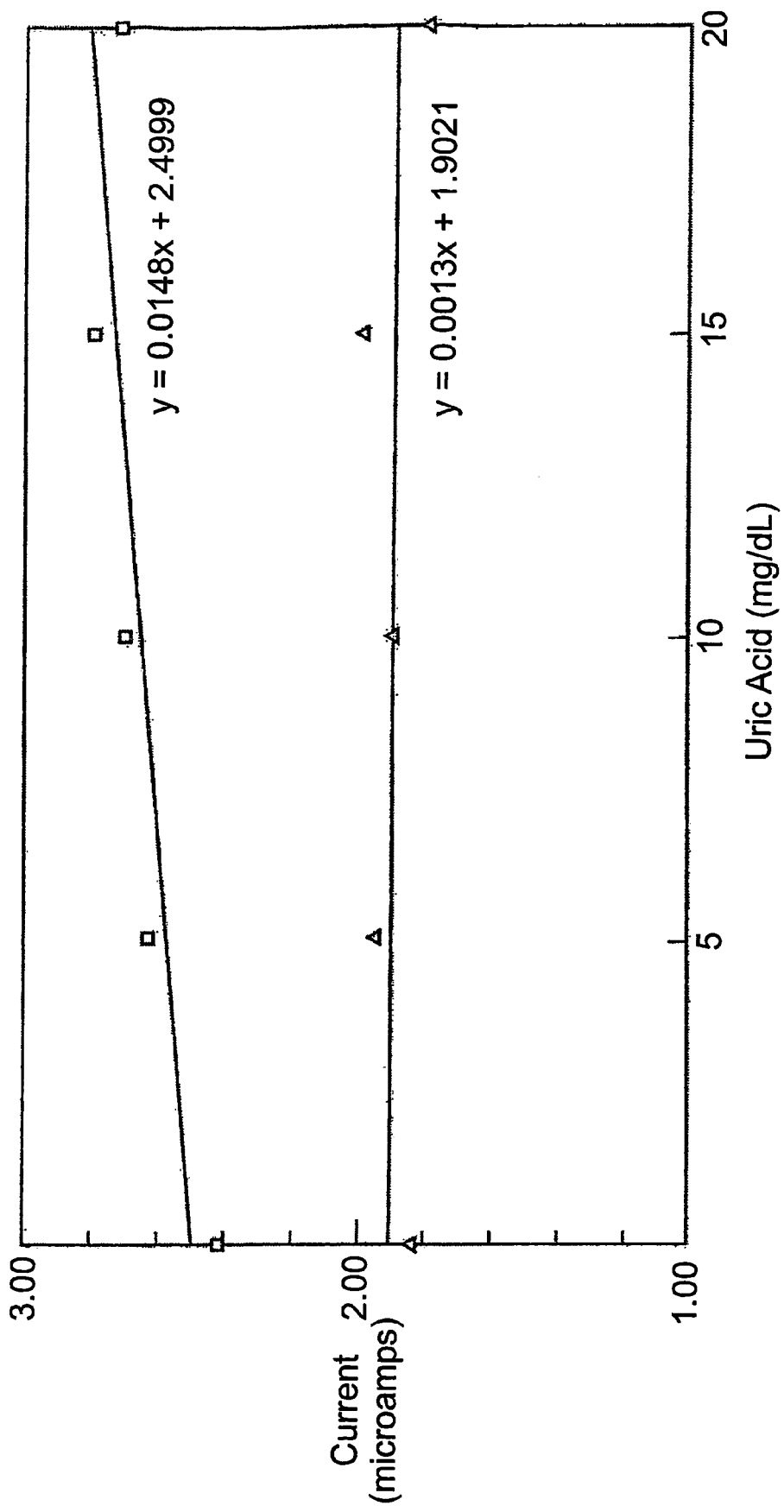
FIG. 12 is a graph showing the current at a first working electrode of a strip designed in accordance with the present invention tested with 240 mg/dL glucose samples in blood spiked with varying levels of uric acid.

FIG. 12 shows the current responses of the first working electrode tested with 240 mg/dL glucose samples in blood spiked with varying levels of uric acid. The purpose of testing strips at 240 mg/dL glucose is to show that the correction algorithm of Equation 7a is also valid over a range of glucose concentrations. Similar to FIG. 11, the uncorrected current at the first working electrode (depicted by squares) shows an increase in current that is proportional to the uric acid concentration. However, the corrected current (depicted by triangles) shows no effect from the increasing uric acid concentration.

Example 2

To show that the method of correcting the current for interferents applies to a wide variety of interferents, strips built according to the embodiment of FIG. 1 were also tested with acetaminophen and gentisic acid at various concentration levels, in addition to uric acid. For purposes of quantitating the magnitude of this effect, a change in glucose output of greater than 10% (for glucose level >70 mg/dL) or 7 mg/dL (for glucose level <=70 mg/dL) was defined as a significant interference. Table 1 shows that the uncorrected current at the first working electrode shows a significant interferent effect at a lower interferent concentration than strips tested with a corrected current response using Equation 7a. This shows that the method of correcting the current output of the first working electrode using Equation 7a is effective in correcting for interferences. Table 1 shows that the current correction in Equation 7a is effective for interferences with respect to acetaminophen, gentisic acid, and uric acid. Table 1 also shows the concentration range of the interferent which is normally found in blood. In addition, Table 1 also shows that the current correction in Equation 7a is effective at 240 mg/dL glucose concentration level.

Figure 13:
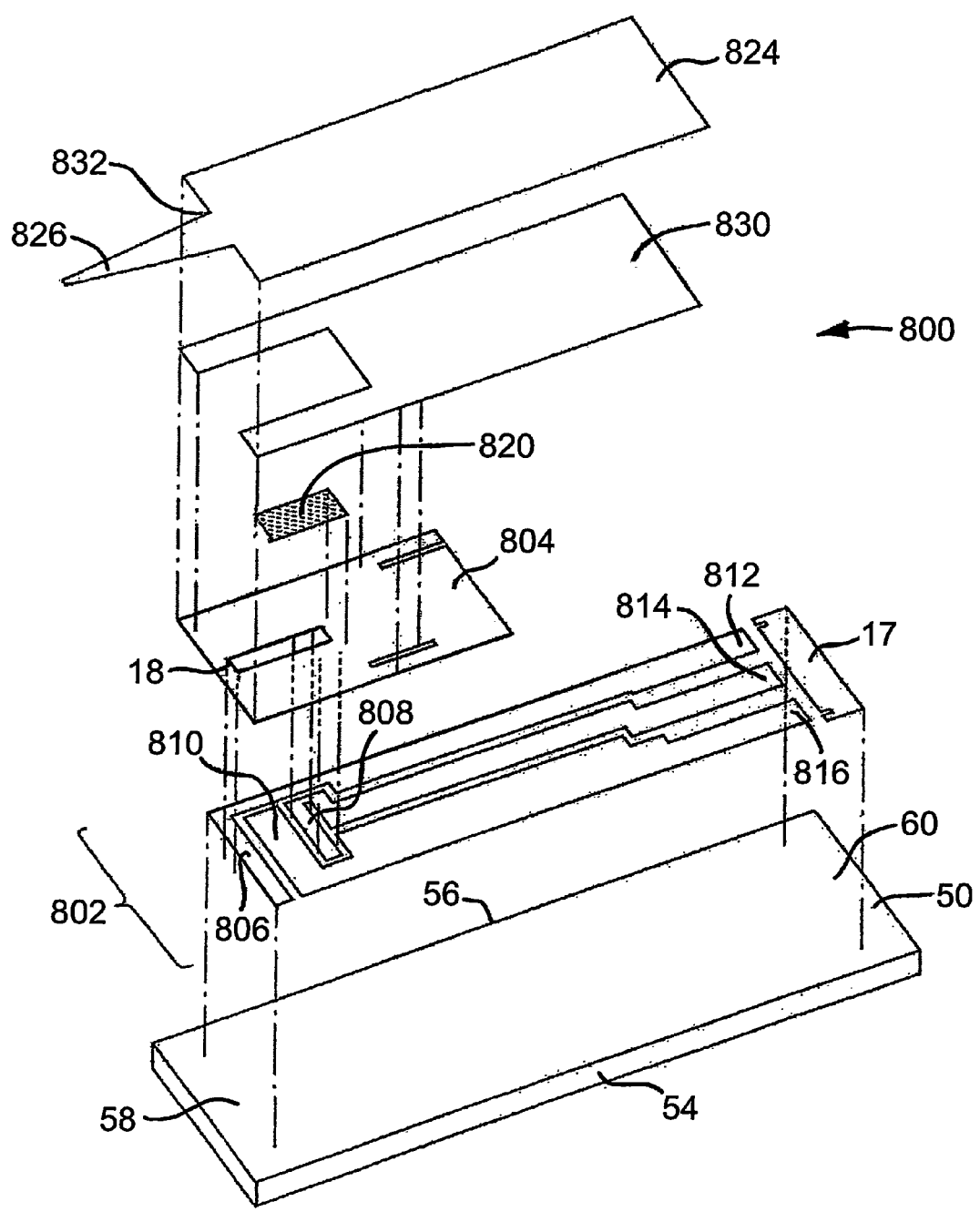
FIG. 13 is an exploded perspective view of a test strip that has an integrated lance.

FIG. 13 shows an exploded perspective view of a test strip 800 that is designed to lance a user's skin layer so as cause physiological fluid to be expressed and collected into test strip 800 in a seamless manner. Test strip 800 includes a substrate 50, a conductive layer 802, an insulation layer 804, a reagent layer 820, an adhesive layer 830, and a top layer 824. Test strip 800 further includes a distal end 58 and a proximal end 60.

In test strip 800, conductive layer 802 is the first layer disposed on substrate 50. Conductive layer 802 includes a second working electrode 806, a first working electrode 808, a reference electrode 810, a second contact 812, a first contact 814, a reference contact 816, a strip detection bar 17, as shown in FIG. 13. The material used for conductive layer 802 and the process for printing conductive layer 802 is the same for both test strip 62 and test strip 800.

Insulation layer 804 is the second layer disposed on substrate 50. Insulation layer 16 includes a cutout 18 which may have a rectangular shaped structure. Cutout 18 exposes a portion of second working electrode 806, first working electrode 808, and reference electrode 810 which can be wetted with a liquid. The material used for insulation layer 804 and the process for printing insulation layer 804 is the same for both test strip 62 and test strip 800.

Reagent layer 820 is the third layer disposed on substrate 50, first working electrode 808 and reference electrode 810. The material used for reagent layer 820 and the process for printing reagent layer 820 is the same for both test strip 62 and test strip 800.

Adhesive layer 830 is the fourth layer disposed on substrate 50. The material used for adhesive layer 830 and the process for printing adhesive layer 830 is the same for both test strip 62 and test strip 800. The purpose of adhesive layer 830 is to secure top layer 824 to test strip 800. In an embodiment of this invention, top layer 824 may be in the form of an integrated lance as shown in FIG. 13. In such an embodiment, top layer 824 may include a lance 826 which is located at distal end 58.

Lance 826, which may also be referred to as a penetration member, may be adapted to pierce a user's skin and draw blood into test strip 800 such that second working electrode 806, first working electrode 808, and reference electrode 810 are wetted. Lance 826 includes a lancet base 832 that terminates at distal end 58 of the assembled test strip. Lance 826 may be made with either an insulating material such as plastic, glass, and silicon, or a conducting material such as stainless steel and gold. Further descriptions of integrated medical devices that use an integrated lance can be found in International Application No. PCT/GB01/05634 and U.S. patent application Ser. No. 10/143,399. In addition, lance 826 can be fabricated, for example, by a progressive die-stamping technique, as disclosed in the aforementioned International Application No. PCT/GB01/05634 and U.S. patent application Ser. No. 10/143,399.

Figure 14:
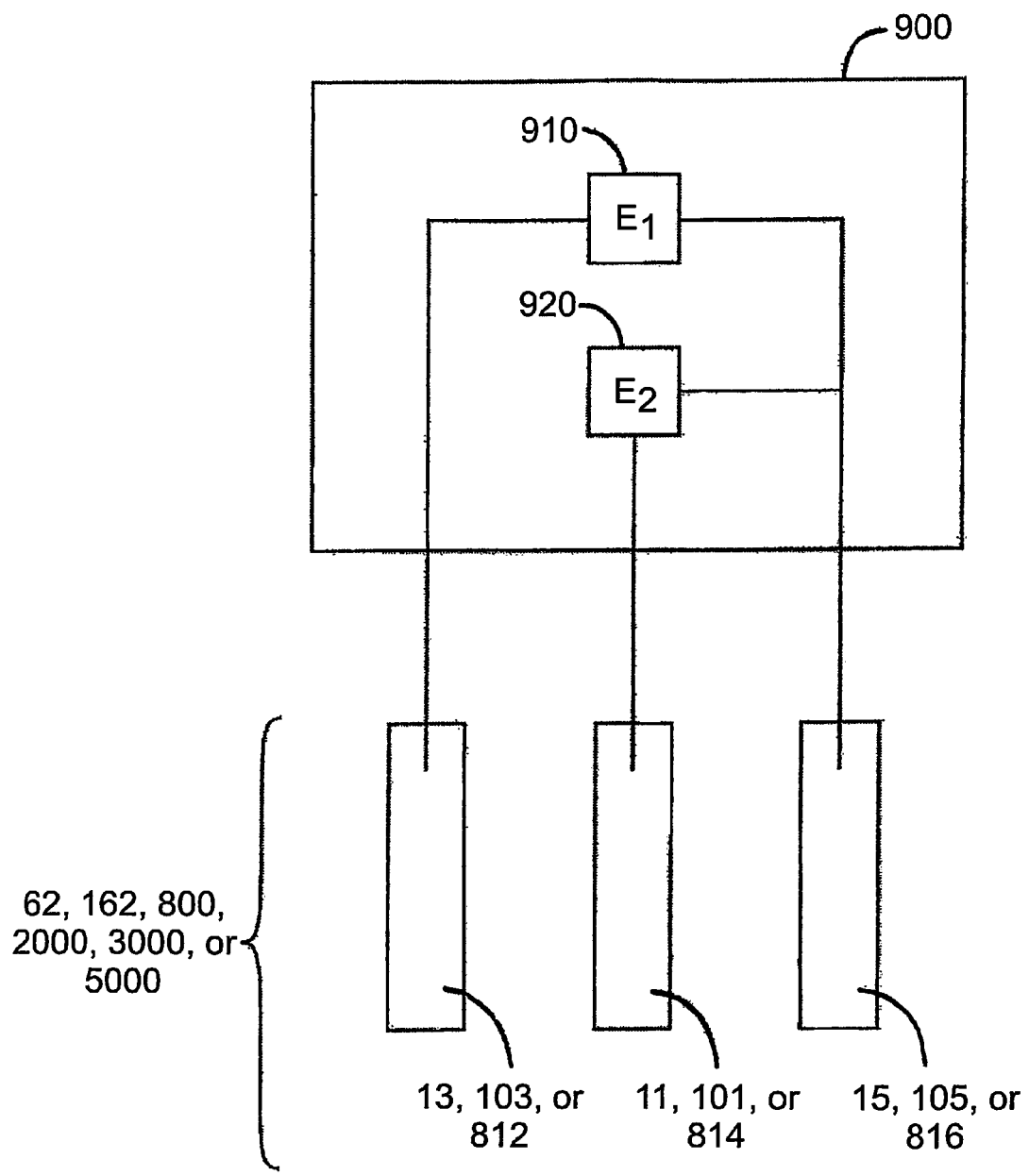
FIG. 14 is a simplified schematic showing a meter interfacing with a test strip that has a first contact, second contact, and reference contact disposed on a substrate.

FIG. 14 is a simplified schematic showing a meter 900 interfacing with a test strip. In an embodiment of this invention the following test strips may be suitable for use with meter 900 which are test strip 62, test strip 162, test strip 800, test strip 2000, test strip 3000, or test strip 5000. Meter 900 has at least three electrical contacts that form an electrical connection to the second working electrode, the first working electrode, and the reference electrode. In particular second contact (13, 103, or 812) and reference contact (15, 105, or 816) connect to a first voltage source 910; first contact (11, 101, or 814) and the reference contact (15, 105, or 816) connect to a second voltage source 920.

When performing a test, first voltage source 910 applies a first potential E1 between the second working electrode and the reference electrode; and second voltage source 920 applies a second potential E2 between the first working electrode and the reference electrode. In one embodiment of this invention, first potential E1 and second potential E2 may be the same such as for example about +0.4 V. In another embodiment of this invention, first potential E1 and second potential E2 maybe different. A sample of blood is applied such that the second working electrode, the first working electrode, and the reference electrode are covered with blood. This allows the second working electrode and the first working electrode to measure a current which is proportional to glucose and/or non-enzyme specific sources. After about 5 seconds from the sample application, meter 900 measures an oxidation current or both the second working electrode and the first working electrode.

TABLE 1

Summary of Interference Performance Using Uncorrected and Corrected Current Output

| Mode | Interferent | Glucose Concentration (mg/dL) | Inteferent Concentration where effect is signficant | Normal Concentration range of interferent |
|---|---|---|---|---|
| Uncorrected | Acetaminophen | 70 | 11 | 1-2 |
| Uncorrected | Gentisic Acid | 70 | 10 | 0.05-0.5 |
| Uncorrected | Uric Acid | 70 | 5 | 2.6-7.2 |
| Uncorrected | Acetaminophen | 240 | 16 | 1-2 |
| Uncorrected | Gentisic Acid | 240 | 12 | 0.05-0.5 |
| Uncorrected | Uric Acid | 240 | 8 | 2.6-7.2 |
| Corrected | Acetaminophen | 70 | 120 | 1-2 |
| Corrected | Gentisic Acid | 70 | 47 | 0.05-0.5 |
| Corrected | Uric Acid | 70 | 33 | 2.6-7.2 |
| Corrected | Acetaminophen | 240 | 59 | 1-2 |
| Corrected | Gentisic Acid | 240 | 178 | 0.05-0.5 |
| Corrected | Uric Acid | 240 | 29 | 2.6-7.2 |

What is claimed is:

1. A method of reducing interferences in an electrochemical sensor comprising:
   measuring a first current using a first working electrode, said first working electrode having an area being covered by a reagent layer;
   measuring a second current using a second working electrode having a covered area coated by the reagent layer and an uncovered area not coated by the reagent layer such that intereferent current produced at the uncovered area is proportional to interferent current produced overall; and
   calculating, by a meter, a corrected current value representative of a glucose concentration using the measured first current, the measured second current, and a ratio of said covered area to said uncovered area of said second working electrode to reduce the effects of interferents.

2. The method of claim 1, wherein said corrected current value is calculated using the equation:

$$G = WE_1 - \left\{ \left( \frac{A_{cov}}{A_{unc}} \right) \times (WE_2 - WE_1) \right\} \quad \text{(Eq 7a)}$$

where G is the corrected current value, $WE_1$ is the uncorrected current density at said first working electrode, $WE_2$ is the uncorrected current density at said second working electrode, $A_{cov}$ is the coated area of said second working electrode, and $A_{unc}$ is the uncoated area of said second working electrode.

3. The method of claim 1, in which the interferent comprises one or more of acetaminophen, gentisic acid, uric acid, and combinations thereof.

4. A method of reducing interferences in an electrochemical sensor comprising:
   measuring a first current using a first working electrode, wherein said reagent layer partially covers said first working electrode, said first working electrode having a first coated area covered by said reagent layer and a first uncoated area not covered by said reagent layer;
   measuring a second current using a second working electrode, wherein said reagent layer partially covers said second working electrode, said second working electrode having a second covered area coated by said reagent layer and a second uncovered area not coated by said reagent layer such that intereferent current produced at the uncovered area is proportional to interferent current produced overall; and
   calculating, by a meter, a corrected current value representative of a glucose concentration using the measured first current, the measured second current, and a ratio of said covered area to said uncovered area of said first and said second working electrodes to reduce the effects of interferents.

5. The method of claim 4, wherein said corrected current value is calculated using the equation:

$$G = WE_1 - \left\{ \left( \frac{f_1 + f_2}{f_2 - 1} \right) \times (WE_2 - WE_1) \right\} \quad \text{(Eq 7c)}$$

where $$f_1 = \frac{A_{cov1}}{A_{unc1}};$$

$$f_2 = \frac{A_{cov1}}{A_{unc2}};$$

$A_{unc1}$ is an uncoated area of said first working electrode;
$A_{unc2}$ is an uncoated area of said second working electrode;
$A_{cov1}$ is a coated area of said first working electrode;
$A_{cov2}$ is a coated area of said second working electrode;
G is the corrected current value;
$WE_1$ is the uncorrected current density at said first working electrode; and
$WE_2$ is the uncorrected density at said second working electrode.

6. The method of one of claim 1 or claim 4, in which the interferent comprises one or more of acetaminophen, gentisic acid, uric acid, and combinations thereof.

7. A method of reducing interferences in an electrochemical sensor having a first and second working electrodes disposed on a substrate and an insulation disposed over electrodes and the substrate, the insulation having an opening to allow a reagent to contact portions of the first and second working electrodes, the method comprising:
   measuring a first current using a first working electrode, said first working electrode having an area coated by the reagent;
   measuring a second current using a second working electrode having an area coated by the reagent and an area uncoated by the reagent such that intereferent current produced at the uncoated area is proportional to interferent current produced overall; and calculating, by a meter, a corrected current value representative of a glucose concentration using the measured first current, the measured second current, and a ratio of said coated area to said uncoated area of said second working electrode to reduce the effects of interferents.

8. The method of claim 7, in which said corrected current value is calculated using the equation:

$$G = WE_1 - \left\{\left(\frac{A_{cov}}{A_{unc}}\right) \times (WE_2 - WE_1)\right\}$$

where G is the corrected current value, $WE_1$ is the uncorrected current at said first working electrode, $WE_2$ is the uncorrected current at said second working electrode, $A_{cov}$ is the coated area of said second working electrode, and $A_{unc}$ is the uncoated area of said second working electrode.

9. A method of reducing interferences in an electrochemical sensor having a first and second working electrodes disposed on a substrate and an insulation disposed over electrodes and the substrate, the insulation having an opening to allow a reagent to contact portions of the first and second working electrodes, the method comprising:

measuring a first current at using first working electrode having a first coated area covered by the reagent and a first uncoated area not covered by the reagent;

measuring a second current using a second working electrode having a second covered area coated by said reagent and a second uncovered area not coated by said reagent such that intereferent current produced at the uncovered area is proportional to interferent current produced overall; and calculating, by a meter, a corrected current value representative of a glucose concentration using the measured first current, the measured second current, and a ratio of said covered area to said uncovered area of said first and said second working electrodes to reduce the effects of interferents.

10. The method of claim 9, wherein said corrected current value is calculated using the equation:

$$G = WE_1 - \left\{\left(\frac{f_1 + f_2}{f_2 - 1}\right) \times (WE_2 - WE_1)\right\} \quad \text{(Eq 7c)}$$

where $$f_1 = \frac{A_{cov1}}{A_{unc1}};$$

$$f_2 = \frac{A_{cov1}}{A_{unc2}};$$

$A_{unc1}$ is an uncoated area of said first working electrode;

$A_{unc2}$ is an uncoated area of said second working electrode;

$A_{cov1}$ is a coated area of said first working electrode;

$A_{cov2}$ is a coated area of said second working electrode;

G is the corrected current value;

$WE_1$ is the uncorrected current density at said first working electrode; and $WE_2$ is the uncorrected density at said second working electrode.

* * * * *

UNITED STATES PATENT AND TRADEMARK OFFICE
CERTIFICATE OF CORRECTION

PATENT NO.       : 7,653,492 B2                                   Page 1 of 1
APPLICATION NO. : 10/577586
DATED            : January 26, 2010
INVENTOR(S)      : Davies et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 62 days.

Signed and Sealed this

Fourth Day of January, 2011

David J. Kappos
*Director of the United States Patent and Trademark Office*